(12) United States Patent
Leung et al.

(10) Patent No.: US 12,011,279 B2
(45) Date of Patent: Jun. 18, 2024

(54) ELECTRO-ANATOMIC MAPPING SYSTEM

(71) Applicant: Boston Scientific Medical Device Limited, Galway (IE)

(72) Inventors: Jackie Leung, Richmond Hill (CA); Gareth Davies, Toronto (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 322 days.

(21) Appl. No.: 17/223,088

(22) Filed: Apr. 6, 2021

(65) Prior Publication Data

US 2021/0307671 A1    Oct. 7, 2021

Related U.S. Application Data

(60) Provisional application No. 63/006,391, filed on Apr. 7, 2020.

(51) Int. Cl.
| | |
|---|---|
| *G06T 7/00* | (2017.01) |
| *A61B 5/00* | (2006.01) |
| *A61B 5/367* | (2021.01) |
| *G06T 5/70* | (2024.01) |
| *G06T 11/00* | (2006.01) |
| *G16H 40/67* | (2018.01) |

(52) U.S. Cl.
CPC .......... *A61B 5/367* (2021.01); *A61B 5/7203* (2013.01); *G06T 5/70* (2024.01); *G06T 11/00* (2013.01); *G16H 40/67* (2018.01); *A61B 5/4836* (2013.01); *G06T 2207/30048* (2013.01); *G06T 2210/41* (2013.01)

(58) Field of Classification Search
CPC .................................................. A61B 5/367
USPC ........................................................ 600/523
See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |

(Continued)

*Primary Examiner* — Nicole F Lavert
*Assistant Examiner* — Nicole F Johnson
(74) *Attorney, Agent, or Firm* — Nelson Mullins Riley & Scarborough LLP

(57) ABSTRACT

An electro-anatomic mapping system is configured, in accordance with a preferred embodiment (and not limited thereto) to: (A) receive a first reference response signal from a first medical device, in which the first reference response signal is configured to be utilized by the electro-anatomic mapping system for formation of a first medical image; and (B) receive a second reference response signal from the first medical device, in which the second reference response signal is configured to be utilized by the electro-anatomic mapping system for forming a second medical image, and in which the second medical image, in use, depicts image noise interference resulting from activation of a second medical device.

20 Claims, 7 Drawing Sheets

(56) References Cited

U.S. PATENT DOCUMENTS

| | | |
|---|---|---|
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | Mcgee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |

(56) References Cited

U.S. PATENT DOCUMENTS

| | | |
|---|---|---|
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | Mcguckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | Mcmichael et al. |
| 2004/0015162 A1 | 1/2004 | Mcgaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | Mcclurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1* | 10/2013 | Mathur ............... A61B 18/1492 607/101 |
| 2013/0293578 A1* | 11/2013 | Leung ................... A61B 34/20 345/633 |
| 2013/0304407 A1* | 11/2013 | George ................ A61B 5/7246 702/72 |
| 2014/0206987 A1 | 7/2014 | Urbanski et al. |
| 2014/0296769 A1 | 10/2014 | Hyde et al. |
| 2015/0066007 A1* | 3/2015 | Srivastava ......... A61B 18/1492 606/41 |
| 2015/0150472 A1* | 6/2015 | Harlev ................. A61B 5/4848 600/374 |

(56) References Cited

U.S. PATENT DOCUMENTS

| | | |
|---|---|---|
| 2016/0220741 A1 | 8/2016 | Garrison et al. |
| 2019/0021763 A1 | 1/2019 | Zhou et al. |
| 2019/0247035 A1 | 8/2019 | Gittard et al. |

* cited by examiner

ELECTRO-ANATOMIC MAPPING SYSTEM

TECHNICAL FIELD

This document relates to the technical field of (and is not limited to) an electro-anatomic mapping system, a non-transitory computer-readable medium for utilization by an electro-anatomic mapping system, and/or a method of utilizing an electro-anatomic mapping system.

BACKGROUND

Known electro-anatomic mapping (EAM) systems are configured to facilitate the mapping of the interior of a patient, such as the heart of the patient and/or a medical procedure, such as a cardiac ablation procedure. Cardiac ablation is a procedure that is used to scar small areas in the heart of a patient.

SUMMARY

It will be appreciated that there exists a need to mitigate (at least in part) at least one problem associated with the existing or known anatomical mapping systems (also called the existing or known technology). After much study of, and experimentation with, the existing or known anatomical mapping systems, an understanding (at least in part) of the problem and its solution have been identified (at least in part) and are articulated (at least in part) as follows: An electro-anatomic mapping system (EAM system) enables real-time three-dimensional (3D) visualization of intravascular catheters in the heart (preferably without exposure to radiation, for the safety). However, catheter probe tracking may be disrupted when sufficient electromagnetic noise is introduced into the environment, such as during electromagnetic puncture or ablation (such as radio frequency puncture, etc.).

Signal processing dictates that an input consists of signal and noise. Subtraction of the noise from the input leaves only the desired signal. The challenge is usually determining the noise to perform this subtraction. In the case of EAM, a sensor in a fixed position may have a predictable signal, thus any noise added to it can easily be isolated. If the noise originated from a known source of finite duration, it may have a similar effect on all sensors nearby, fixed or otherwise.

It may be desirable to provide an electro-anatomic mapping system with a reference sensor that is fixed in place relative to the heart anatomy. Because it does not move, the signal measured by the sensor is predictable, and any new and/or unexpected received inputs may be isolated as noise. The noise component can be fed into the EAM system to determine the optimal filter for removing said noise in the other catheter signals.

It may be desirable to provide an electro-anatomic mapping system configured to reduce signal noise and thereby improve, at least in part, image quality.

It may be desirable to provide an electro-anatomic mapping system with medical devices (such as catheters with sensors configured to detect electromagnetic signals) along with a noise filtering device or method, etc.

It may be desirable to provide an electro-anatomic mapping system configured to provide spatial tracking of the sensors. The noise filtering method or device may be included in the electro-anatomic mapping system. The medical devices may include a catheter, and/or an intracardiac catheter with distal coils configured to receive electromagnetic signals from the electro-anatomic mapping system. The catheter may be connected to the electro-anatomic mapping system such that received signals may be fed directly back to the electro-anatomic mapping system. The catheter may be part of the clinical workflow for a procedure. For instance, the medical device may include any type of catheter compatible with the electro-anatomic mapping system. This may include, and is not limited to, a sheath, a dilator, a needle, a probe, a wire and/or an external patch device, etc. The electro-anatomic mapping system is configured to receive measurements from a reference sensor for the purpose of isolating a noise component (an unwanted signal). The electro-anatomic mapping system is configured to receive a (clean) signal in the absence of noise from another medical device (such as, a radio frequency puncture device or RF puncture device). The signal may be predictable as long as the sensor position remains relatively stationary. It will be appreciated that adaptive noise cancellation may be utilized on the signals, as may be described in a document titled: ADAPTIVE NOISE CANCELLING: PRINCIPLES AND APPLICATIONS (B. Widrow et al., Proceedings of the IEEE, vol. 63, no. 12, pp. 1692-1716, Dec. 1975,). The reference input may be created by, for instance, a subtraction method (operation), etc.

To mitigate, at least in part, at least one problem associated with the existing technology, there is provided (in accordance with a major aspect) an apparatus. The apparatus comprises an electro-anatomic mapping system, including a processor assembly. A non-transitory computer-readable storage medium includes computer-executable instructions executable by the processor assembly (this is done in such a way that the processor assembly is urged to perform operations). The operations may include waiting for confirmation that a first medical device is positioned at the first stationary position located proximate to a biological wall of a patient. The operations may further include transmitting, once the confirmation has been received, a first reference signal to the first medical device while the first medical device is kept positioned at the first stationary position The operations may further include receiving a first reference response signal from the first medical device while the first medical device is kept positioned at the first stationary position. The first medical device transmits, in use, the first reference response signal to the electro-anatomic mapping system in response to the first medical device receiving, in use, the first reference signal from the electro-anatomic mapping system. The first reference response signal is configured to be utilized by the electro-anatomic mapping system for formation of a first medical image (to be depicted on a display device of the electro-anatomic mapping system). The electro-anatomic mapping system is configured to superimpose the location of the sensors onto an existing (pre-existing) medical image of the anatomy (of a patient), similar to the manner in which a computerized tomography (CT) scanner may acquire (before the procedure is started). Therefore, it will be appreciated that the term "formation of a medical image" may include the superimposition of the location (the detected location) of the sensors onto an existing (pre-existing) medical image of the anatomy, similar to the manner in which a computerized tomography (CT) scanner may acquire (before the procedure is started). The operations may further include waiting for confirmation that a second medical device is positioned, and activated, at a noise-source position located relative to the first stationary position and located relative to the biological wall of the patient (while the first medical device is kept positioned at the first stationary position). The operations may further include waiting for confirmation that the second medical device transmitted, in use, a second medical-device signal toward the first medical device while the first medical device is kept positioned at the first stationary position and while the second medical device is kept positioned at the noise-source position.

To mitigate, at least in part, at least one problem associated with the existing technology, there is provided (in accordance with a major aspect) an apparatus. The apparatus includes a non-transitory computer-readable medium having (including) computer-executable instructions that, when executed by a processor assembly of an electro-anatomic mapping system, causes the processor assembly to perform operations. The operations include waiting for confirmation that a first medical device is positioned at the first stationary position located proximate to a biological wall of a patient. The operations further include transmitting, once the confirmation has been received, a first reference signal to the first medical device while the first medical device is kept positioned at the first stationary position. The operations further include receiving a first reference response signal from the first medical device while the first medical device is kept positioned at the first stationary position. The first medical device transmits, in use, the first reference response signal to the electro-anatomic mapping system in response to the first medical device receiving, in use, the first reference signal from the electro-anatomic mapping system. The first reference response signal is configured to be utilized by the electro-anatomic mapping system for formation of a first medical image (to be depicted on a display device of the electro-anatomic mapping system). The operations further include waiting for confirmation that a second medical device is positioned, and activated, at a noise-source position located relative to the first stationary position and located relative to the biological wall of the patient (while the first medical device is kept positioned at the first stationary position). The operations further include waiting for confirmation that the second medical device transmitted, in use, a second medical-device signal toward the first medical device while the first medical device is kept positioned at the first stationary position and while the second medical device is kept positioned at the noise-source position.

To mitigate, at least in part, at least one problem associated with the existing technology, there is provided (in accordance with a major aspect) a method. The method is for utilizing an electro-anatomic mapping system. The method includes waiting for confirmation that a first medical device is positioned at the first stationary position located proximate to a biological wall of a patient. The method also includes transmitting, once the confirmation has been received, a first reference signal to the first medical device while the first medical device is kept positioned at the first stationary position. The method also includes receiving a first reference response signal from the first medical device while the first medical device is kept positioned at the first stationary position, in which the first medical device transmits, in use, the first reference response signal to the electro-anatomic mapping system in response to the first medical device receiving, in use, the first reference signal from the electro-anatomic mapping system. The first reference response signal is configured to be utilized by the electro-anatomic mapping system for formation of a first medical image to be depicted on a display device of the electro-anatomic mapping system. The method also includes waiting for confirmation that a second medical device is positioned, and activated, at a noise-source position located relative to the first stationary position and located relative to the biological wall of the patient (while the first medical device is kept positioned at the first stationary position). The method also includes waiting for confirmation that the second medical device transmitted, in use, a second medical-device signal toward the first medical device while the first medical device is kept positioned at the first stationary position and while the second medical device is kept positioned at the noise-source position.

To mitigate, at least in part, at least one problem associated with the existing technology, there is provided (in accordance with a major aspect) an apparatus. The apparatus comprises an electro-anatomic mapping system, including a processor assembly; and a non-transitory computer-readable storage medium including computer-executable instructions being executable by the processor assembly in such a way that the processor assembly, of the electro-anatomic mapping system, is urged to perform operations, including: a transmitting operation including transmitting (in use) a first reference signal to a first medical device; and in response, the first medical device transmits a first reference response signal back to the electro-anatomic mapping system; and a receiving operation including receiving, in use, the first reference response signal from the first medical device; and a computing operation, including computing a reference signal model A, in which the reference signal model A represents the first reference response signal; and a transmitting operation including transmitting the first reference signal to the first medical device, in which a second medical device is positioned proximate to the biological wall of the patient, and in which the second medical device is activated for forming a hole through the biological wall, and in which the second medical device transmits, once activated, a second medical-device signal to the first medical device while the first reference signal continues to be transmitted to the first medical device, and the first medical device receives both the first reference signal from the electro-anatomic mapping system and the second medical-device signal from the second medical device, and in response to receiving both signals, the first medical device transmits a second reference response signal back to the electro-anatomic mapping system; and a receiving operation including receiving, in use, the second reference response signal from the first medical device; and a reading operation including reading, in response to the second medical device being activated, the reference signal model A; and a computing operating including computing the noise-correction datum by evaluating the second reference response signal with the reference signal model A. The apparatus may further be adapted such that a computing operating includes computing a noise filter (F) based on the noise-correction datum, in which the noise filter (F) is configured to remove, at least in part, the contribution of the second medical-device signal from the medical image to be formed or generated and displayed by the electro-anatomic mapping system. The apparatus may further be adapted such that the computer-executable instructions further urge the processor assembly to perform an applying operation including applying the filter (F) to remove the noise originating from the second medical device and transmitted through other medical device assemblies.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
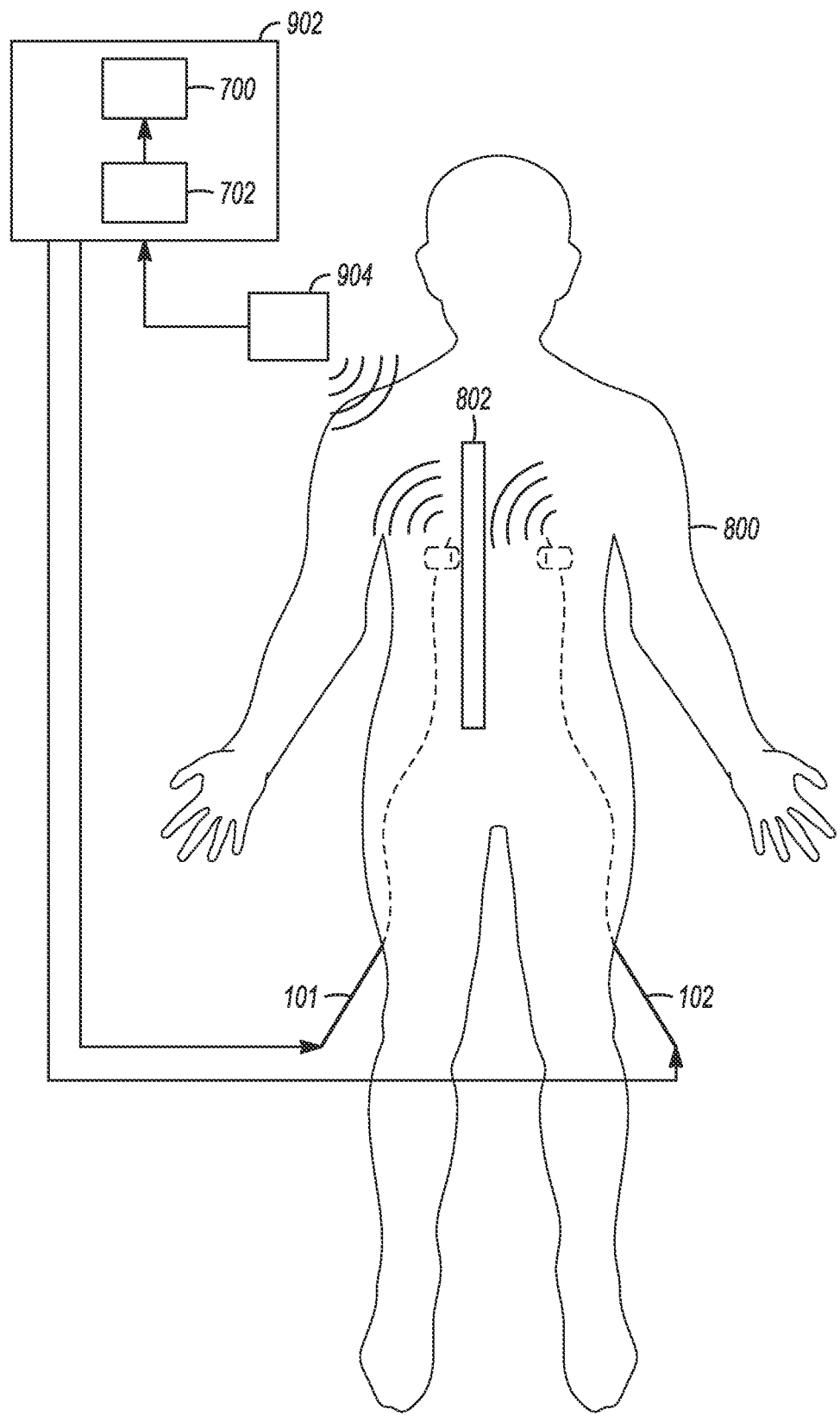
FIG. 1 to FIG. 12 depict schematic views of an electro-anatomic mapping system.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS first medical device 101
second medical device 102
third medical device 103
fourth medical device 104
fifth medical device assembly 105
first stationary position 201
noise-source position 202
proximate position 204
wall-contact position 206
second medical-device signal 302
noise-correction datum 304
first reference signal 401
reference signal model 501A
first reference response signal 501
second reference response signal 502
third reference response signal 503
fourth reference response signal 504
operations 602 to 620
processor assembly 700
non-transitory computer-readable storage medium 702
patient 800
biological wall 802
wall passageway 804
electro-anatomic mapping system 902
sensor-interface system 904

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

FIG. 1 to FIG. 12 depict schematic views of an electro-anatomic mapping system 902.

Figure 13:
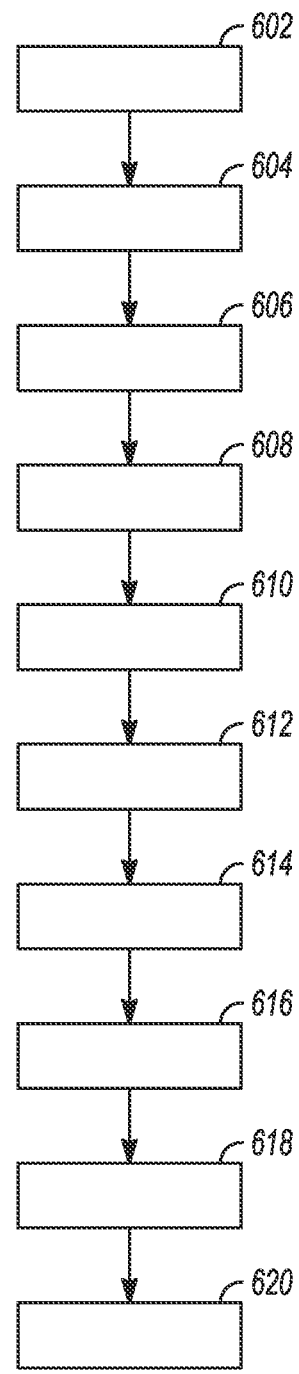
FIG. 13 depicts a schematic view of computer-executable instructions tangibly stored in a non-transitory computer-readable storage medium configured to urge a processor assembly to perform various operations associated with the electro-anatomic mapping system of FIG. 1.

FIG. 13 depicts a schematic view of computer-executable instructions tangibly stored in a non-transitory computer-readable storage medium 702 configured to urge a processor assembly 700 to perform various operations associated with the electro-anatomic mapping system 902 of FIG. 1.

Referring to the embodiment as depicted in FIG. 1, there is depicted an electro-anatomic mapping system 902 including and not limited to (comprising) a processor assembly 700 and a non-transitory computer-readable storage medium 702 including computer-executable instructions that are executable by the processor assembly 700 (this is done in such a way that the processor assembly 700 is urged to perform operations (described below in connection with the other FIGS.). It will be appreciated that the computer-executable instructions may be called software. The non-transitory computer-readable storage medium 702 may be called or include a memory assembly configured to receive and tangibly store the computer-executable instructions (also called an executable program). The computer-executable instructions include coded instructions (programmed coded instructions) configured to be readable by, and executable by, the processor assembly 700. The computer-executable instructions are configured to urge the processor assembly 700 to perform predetermined processor operations. Equivalents to the computer-executable instructions may include: (A) an application-specific integrated circuit and any equivalent thereof, (B) a field-programmable gate array (FPGA), (C) machine-language code, (D) assembly-language code, and/or (E) source code formed in a high-level computing language understood by humans, and any equivalent thereof. The high-level language of the source code is compiled into either an executable machine code file or a non-executable machine-code object file. It will be appreciated that the computer-executable instructions are predetermined computing steps, computing functions and/or calculations (comparisons, etc.). Computing hardware and other operating components are utilized and are suitable for performing the computing processes of the embodiments and are not intended to limit the applicable environments. A person of skill in the art will immediately appreciate that the embodiments may be practiced with other computer system configurations (including set-top boxes, hand-held devices, multiprocessor systems, microprocessor-based or programmable consumer electronics, network computers, minicomputers, mainframe computers, and the like, and any equivalent thereof). The processor assembly 700 may include, for instance, a conventional microprocessor assembly such as the INTEL (TRADEMARK) PENTIUM (TRADEMARK) microprocessor or the MOTOROLA (TRADEMARK) POWER PC (TRADEMARK) microprocessor. A person of skill in the art will immediately recognize that the term "memory assembly" (also called a computer-readable medium or a machine-readable medium, etc.) may include any type of storage device that is accessible by the processor assembly 700 or by other data processing systems. The non-transitory computer-readable storage medium 702 (also called a memory assembly) may be embodied on a magnetic hard disk or an optical disk having executable instructions to cause the processor assembly 700 to perform computing operations (computing methods, operational steps, computing operations, etc., and/or any equivalent thereof). Computer hardware (operating components and/or any equivalent thereof) suitable for performing the processes of the embodiments are not intended to limit the applicable computing environments. The electro-anatomic mapping system 902 (known to persons skilled in the art and not further described) is configured to be electrically connectable (selectively electrically connectable, coupled) to a sensor-interface system 904 (known to persons skilled in the art and not further described). The sensor-interface system 904 is configured to transmit an electromagnetic-transmission signal to a first medical device 101 and a second medical device 102.

Referring to the embodiment as depicted in FIG. 1, the first medical device 101 is (preferably) configured to be inserted into the patient 800.

Referring to the embodiment as depicted in FIG. 1, the second medical device 102 is (preferably) configured to be inserted into the patient 800.

Referring to the embodiment as depicted in FIG. 1, there is depicted a non-transitory computer-readable storage medium 702 including and not limited to (comprising) computer-executable instructions. The computer-executable instructions are configured so that when executed by a processor assembly 700 of the electro-anatomic mapping system 902, the processor assembly 700 is urged to perform various computing operations (to be described below in connection with the remaining FIGS.)

Referring to the embodiments as depicted in FIG. 2 to FIG. 12, there is described a method (a computer-implemented method). The method, when executed by a processor assembly 700 (as depicted in FIG. 1) of the electro-anatomic mapping system 902 (as depicted in FIG. 1), causes the processor assembly 700 to perform various operations for directing the operations of the electro-anatomic mapping system 902. The method is described in more detail below in connection with remaining FIGS., etc.

Figure 2:
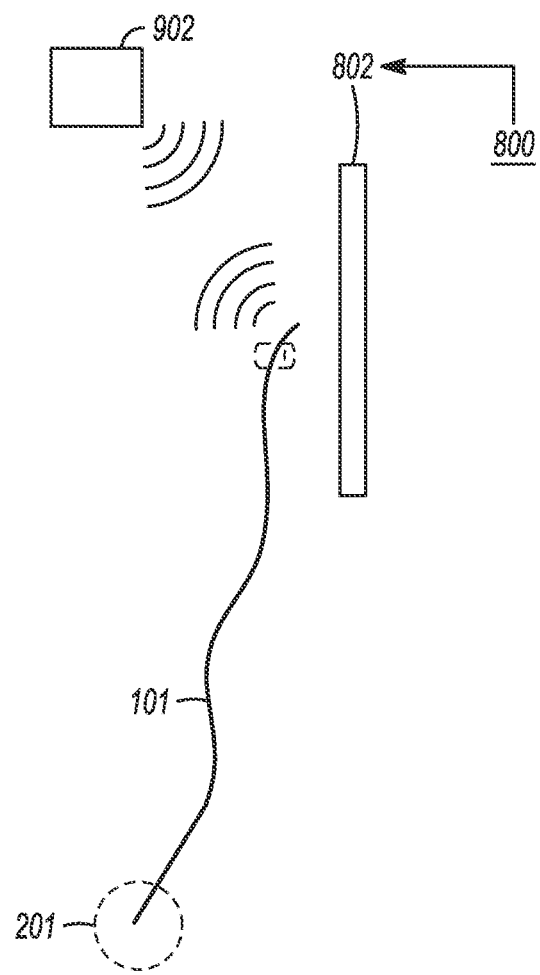

Referring to the embodiment as depicted in FIG. 2, the processor assembly 700 of the electro-anatomic mapping system 902 (which is depicted in FIG. 1) is urged (by the computer-executable instructions tangibly stored in the non-transitory computer-readable storage medium 702) to perform a waiting operation (602), which is depicted in FIG. 13. The waiting operation (602) includes waiting for confirmation that a first medical device 101 is positioned at a first stationary position 201 located proximate to a biological wall 802 of a patient 800. The first medical device 101 remains positioned at the first stationary position 201 (during the procedure).

Figure 3:
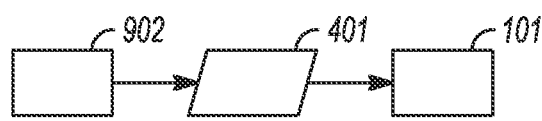

Referring to the embodiments as depicted in FIG. 2 and FIG. 3, the processor assembly 700 of the electro-anatomic mapping system 902 (which is depicted in FIG. 1) is urged (by the computer-executable instructions tangibly stored in the non-transitory computer-readable storage medium 702) to perform a transmitting operation (604), which is depicted in FIG. 13. The transmitting operation (604) includes transmitting (from the electro-anatomic mapping system 902), once the confirmation has been received, a first reference signal 401 to the first medical device 101 (this is done while the first medical device 101 is kept positioned at the first stationary position 201).

Figure 4:
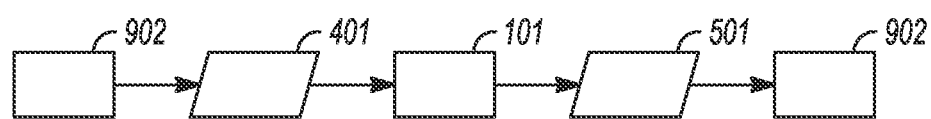
Figure 5:
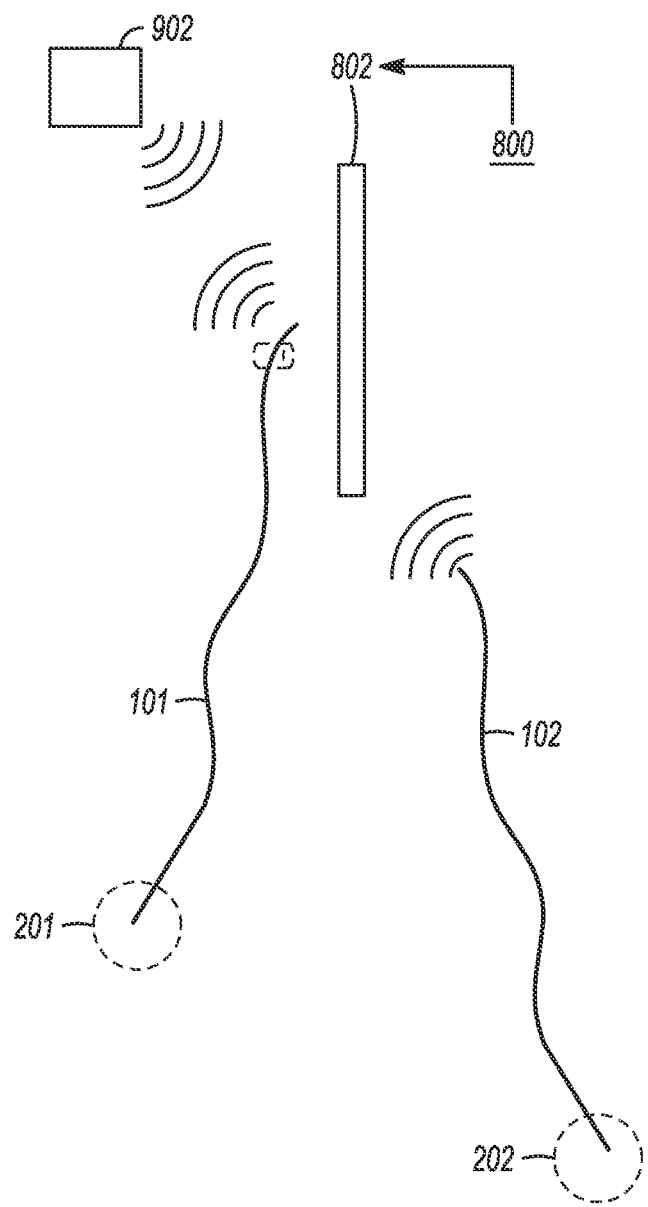

Referring to the embodiments as depicted in FIG. 2 and FIG. 4, the processor assembly 700 of the electro-anatomic mapping system 902 (which is depicted in FIG. 1) is urged (by the computer-executable instructions tangibly stored in the non-transitory computer-readable storage medium 702) to perform a receiving operation (606), which is depicted in FIG. 13. The receiving operation (606) includes receiving a first reference response signal 501 from the first medical device 101 (this is done while the first medical device 101 is kept positioned at the first stationary position 201). The first medical device 101 transmits (in use) the first reference response signal 501 to the electro-anatomic mapping system 902 (this is done in response to the first medical device 101 receiving, in use, the first reference signal 401 from the electro-anatomic mapping system 902). The first reference response signal 501 is configured to be utilized by the electro-anatomic mapping system 902 for formation (in a process for formation of) of a first medical image to be depicted on a display device of the electro-anatomic mapping system 902. It will be appreciated that the transmission of (exchange of) signals may include persistent (continuous) transmissions or may include intermittent transmissions, simultaneous transmissions, near-simultaneous transmissions, etc. and/or any equivalent thereof. It will be appreciated that the order of transmission (sending to, and/or receiving from) of signals between the sensors of the medical device assemblies and the electro-anatomic mapping system 902 does not necessarily require a specific sequenced order of transmission per se. For instance, the electro-anatomic mapping system 902 may be active to aid in the positioning of first medical device 101 and/or second medical device 102. It will be appreciated that during normal operation of the electro-anatomic mapping system 902, the noise component is relatively small. It will be appreciated that, for instance, adaptive noise cancellation may be relevant in the presence of a relatively significant amount of noise component, such as when the radio frequency energy is delivered to a portion of the patient while the medical image is formed by the electro-anatomic mapping system 902. The source of the noise component may not always be present, and that it will become known once the noise component is present (that may interfere with the transmission of signals). It will be appreciated that, in accordance with a preferred embodiment, the noise component includes the signal noise originating from a noise source position of the noise source (such as depicted in FIG. 5), and does not include the background noise. It will be appreciated that, in accordance with a preferred embodiment, the noise component may or may not include background noise that may be, or may not be, persistent (such as, random noise, transient noise, ambient noise, thermal noise, physiological noise, environmental noise and/or any type of noise that does not originate from the noise source position per se). It will be appreciated that the background noise may be relatively smaller in amount (degree) when compared to the noise component originating from the noise source position.

Referring to the embodiment as depicted in FIG. 5, the processor assembly 700 of the electro-anatomic mapping system 902 (which is depicted in FIG. 1) is urged (by the computer-executable instructions tangibly stored in the non-transitory computer-readable storage medium 702) to perform a waiting operation (608), which is depicted in FIG. 13. The waiting operation (608) includes waiting for confirmation that a second medical device 102 is positioned, and activated (such as for a cutting operation, etc.), at a noise-source position 202 (also called a second position or a secondary stationary position) located relative to the first stationary position 201 and located relative to the biological wall 802 of the patient 800 (this is done while the first medical device 101 is kept positioned at the first stationary position 201).

Figure 6:
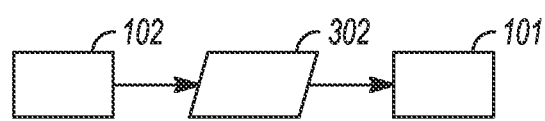

Referring to the embodiments as depicted in FIG. 5 and FIG. 6, the processor assembly 700 of the electro-anatomic mapping system 902 (which is depicted in FIG. 1) is urged (by the computer-executable instructions tangibly stored in the non-transitory computer-readable storage medium 702) to perform a waiting operation (610), which is depicted in FIG. 13. The waiting operation (610) includes waiting for confirmation that the second medical device 102 transmitted (sent) a second medical-device signal 302 toward the first medical device 101 (this is done while the first medical device 101 is kept positioned at the first stationary position 201 and while the second medical device 102 is kept positioned at the noise-source position 202). It will be appreciated that the signal source of the noise component (such as radio frequency noise from and RF cutting device, etc.) need not be stationary per se for the electro-anatomic mapping system 902 to be able to form images. FIG. 5 depicts the signal from the noise component in a stationary position (for a moment in time, for the purposes of illustration and description of an embodiment). The noise component (noise signal) does not need to be stationary per se.

Figure 7:
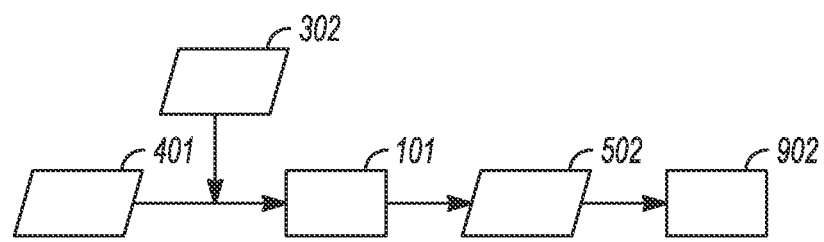

Referring to the embodiments as depicted in FIG. 5 and FIG. 7, the processor assembly 700 of the electro-anatomic mapping system 902 (which is depicted in FIG. 1) is urged (by the computer-executable instructions tangibly stored in the non-transitory computer-readable storage medium 702) to perform a receiving operation (612), which is depicted in FIG. 13. The receiving operation (612) includes receiving a second reference response signal 502 from the first medical device 101. The second reference response signal 502 is configured to be utilized by the electro-anatomic mapping system 902 for forming (in a process for formation of) a second medical image of the biological wall 802 of the patient 800 (the medical image is to be displayed on the display device of the electro-anatomic mapping system 902). The second medical image (in use or as displayed) depicts image noise interference resulting from activation of the second medical device 102 that is positioned at the noise-source position 202 (this is done while the first medical device 101 is kept positioned at the first stationary position). The first medical device 101 transmits, in use, the second reference response signal 502 to the electro-anatomic mapping system 902; this is done in response to the first medical device 101 receiving: (A) the first reference signal 401 from the electro-anatomic mapping system 902, and (B) the second medical-device signal 302 from the second medical device 102.

Figure 8:
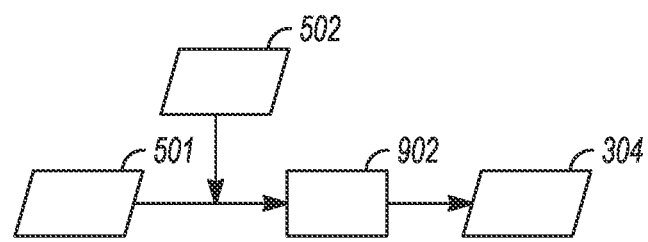

Referring to the embodiments as depicted in FIG. 5 and FIG. 8, the processor assembly 700 of the electro-anatomic mapping system 902 (which is depicted in FIG. 1) is urged (by the computer-executable instructions tangibly stored in the non-transitory computer-readable storage medium 702) to perform a computing operation (614), which is depicted in FIG. 13. The computing operation (614) includes computing a noise-correction datum 304 to be utilized for the generation of a relatively less noisier medical image by the electro-anatomic mapping system 902; the relatively less noisier medical image is a medical image that has a lower degree of noise or signal interference when compared to a previously generated medical image. The noise-correction datum 304 is a result of electromagnetic interference between: (A) the second medical-device signal 302 (which was emitted by the second medical device 102 at the noise-source position 202), and (B) the first medical device 101.

Referring to the embodiment as depicted in FIG. 8, the noise-correction datum 304 is (preferably or by any other equivalent arrangement) computed by a signal processing operation including subtraction between the second reference response signal 502 and the first reference response signal 501.

Figure 9:
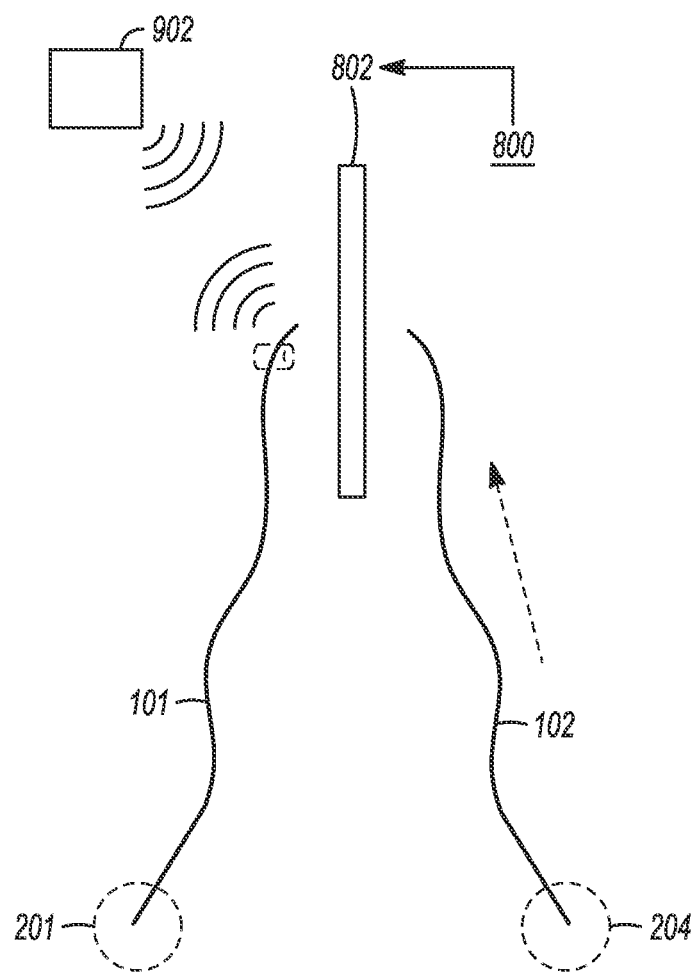

Referring to the embodiment as depicted in FIG. 9, the processor assembly 700 of the electro-anatomic mapping system 902 (which is depicted in FIG. 1) is urged (by the computer-executable instructions tangibly stored in the non-transitory computer-readable storage medium 702) to perform a waiting operation (616), which is depicted in FIG. 13. The waiting operation (616) includes waiting for confirmation that the second medical device 102 is deactivated and moved away from the noise-source position 202 to a proximate position 204 located closer to the biological wall 802 of the patient 800 (this is done while the first medical device 101 is kept positioned at the first stationary position 201). It will be appreciated that the noise source may turned off (if so desired) while the noise source (such as a radio frequency cutting tool) is moved to the biological wall, and that it may be desirable to deactivate the RF cutting tool while the RF cutting tool is moved through the body of the patient, etc.

Figure 10:
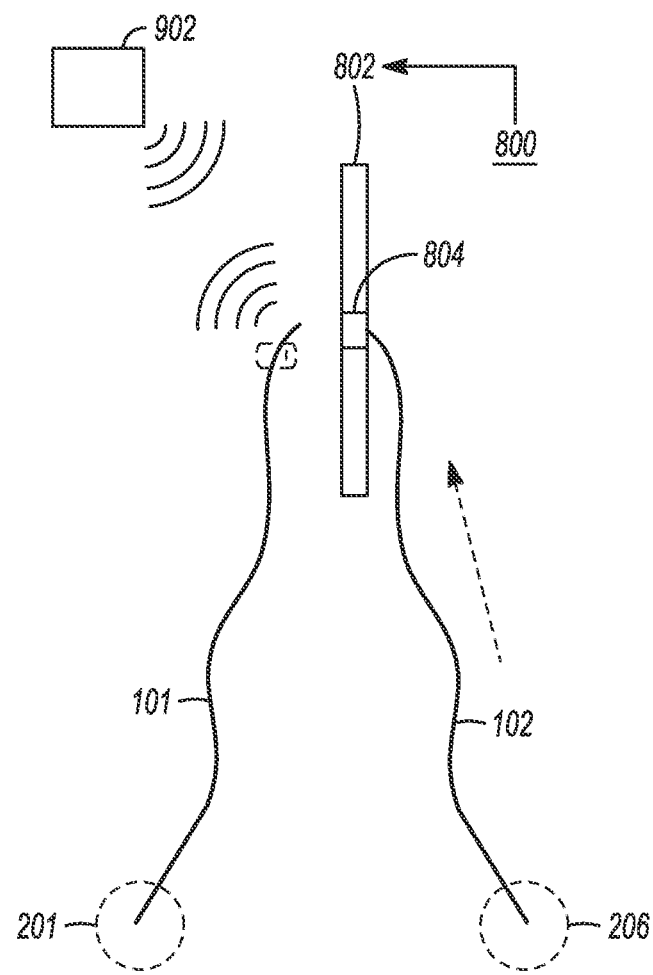
Figure 11:
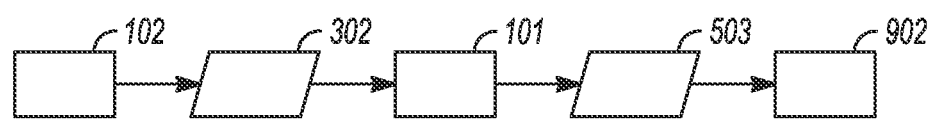

Referring to the embodiment as depicted in FIG. 10 and FIG. 11, the processor assembly 700 of the electro-anatomic mapping system 902 (which is depicted in FIG. 1) is urged (by the computer-executable instructions tangibly stored in the non-transitory computer-readable storage medium 702) to perform a receiving operation (618), which is depicted in FIG. 13. The receiving operation (618) includes receiving a third reference response signal 503 from the first medical device 101 (while the first medical device 101 is kept positioned at the first stationary position 201, and while the second medical device 102 is positioned at a wall-contact position 206 located on a surface of the biological wall 802 of the patient 800). The second medical device 102 is activated (for cutting the wall passageway 804 through the biological wall 802). The first medical device 101 transmits, in use, the third reference response signal 503 in response to the first medical device 101 receiving, in use, the second medical-device signal 302 from the second medical device 102.

Figure 12:
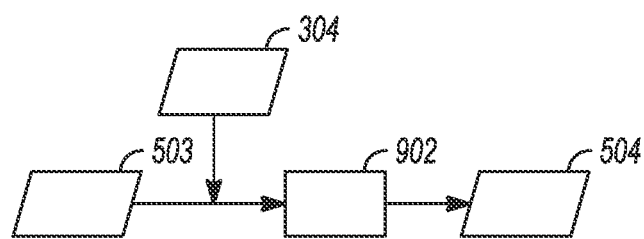

Referring to the embodiment as depicted in FIG. 10 and FIG. 12, the processor assembly 700 of the electro-anatomic mapping system 902 (which is depicted in FIG. 1) is urged (by the computer-executable instructions tangibly stored in the non-transitory computer-readable storage medium 702) to perform a removing operation (620), which is depicted in FIG. 13. The removing operation (620) includes removing, at least in part, signal interference from the third reference response signal 503. The third reference response signal 503 was provided by the first medical device 101 in response to receiving, in use, the second medical-device signal 302. Signal interference was imparted by activation of the second medical device 102 (while positioned at the wall-contact position 206 and while the second medical device 102, in use, is activated to burn or form a wall passageway 804 through the biological wall 802 at the wall-contact position 206). It will be appreciated that noise reduction (or noise cancelation) includes the recovery of the original signal from the noise-corrupted signal (by removal of the noise component). The mathematical limits for the removal of the noise component are set by information theory, namely the Nyquist—Shannon sampling theorem. In signal processing, noise is a general term for unwanted (and, in general, unknown) modifications that a signal may suffer during capture, storage, transmission, processing, or conversion. The electro-anatomic mapping system 902 is configured to reduce, at least in part, the noise component from the noise-corrupted signal and recover, at least in part, the original signal from the noise-corrupted signal (whether the noise component operates under in situ cases or stationary cases, or under non in situ cases or movable cases). It will be appreciated that the electro-anatomic mapping system 902 may utilize any type of noise reduction system, method, algorithm, etc. (and any equivalent thereof) for removing the noise component from a given (detected) signal. It will be appreciated that noise reduction algorithms may tend to alter signals to a greater or lesser degree. For instance, filters may be utilized by the electro-anatomic mapping system 902 in accordance with a specific embodiment. In accordance with a specific embodiment, the electro-anatomic mapping system 902 is configured to generate a filter (electronic filter) that may be utilized in real time (or near-real time) while the radio frequency puncture tool is operating and is moved around in the patient. In accordance with a preferred embodiment, the electro-anatomic mapping system 902 may be configured for real-time (near-real time) noise cancellation (noise reduction) of the noise component. For the case where the noise component is classified as unpredictable (in which case a certain amount of training of the electro-anatomic mapping system 902 may not be suitable). An unpredictable signal is a signal that is random (near random) and may carry (embody) no useful information. The electro-anatomic mapping system 902 is configured to reduce, at least in part, the noise component from the noise-corrupted signal and recover, at least in part, the original signal from the noise-corrupted signal (whether the noise component operates under in situ cases or stationary cases, or under non in situ cases or movable cases). In accordance with a preferred embodiment, the electro-anatomic mapping system 902 may be configured for real-time noise reduction. For the case where the noise component is classified as unpredictable (in which case a certain amount of training of the electro-anatomic mapping system 902 may not be suitable). An unpredictable signal is a signal that is random (near random) and may carry (embody) no useful information. In accordance with a preferred embodiment, the method (for noise reduction) further includes performing real-time noise reduction on the first medical device 101 by removing noise represented by the second medical device 102. In accordance with a preferred embodiment, the electro-anatomic mapping system 902 is configured to perform real-time noise reduction on the first medical device 101 by removing noise represented by the second medical device 102. The fourth reference response signal 504 is computed by a removing operation (620), as depicted in FIG. 12, for removing, at least in part, signal interference from the third reference response signal 503. The fourth reference response signal 504 includes the subtraction between the noise-correction datum 304 and the third reference response signal 503. The fourth reference response signal 504 is configured to be utilized by the electro-anatomic mapping system 902 for the formation of a fourth medical image to be depicted on the display device (of the electro-anatomic mapping system 902), in which noise interference is removed (at least in part) from the fourth medical image. It will be appreciated that the third reference response signal 503 may be utilized with (for manufacturing or computing, etc.) a noise filter. The noise filter may be applied to the noise-correction datum 304 for the purpose of computing the fourth reference response signal 504. The noise filter may include an electronic filter, a digital filter, a software filter (a filter algorithm) usable for digital signal processing computations, and any equivalent thereof. It will be appreciated that noise filters are known to persons of skill in the art and are not further described.

Referring to the embodiment as depicted in FIG. 12, removal, at least in part, of signal interference includes (preferably) subtracting the noise-correction datum 304, which was computed from the third reference response signal 503.

Referring to the embodiment as depicted in FIG. 2, the method includes utilizing (urging, causing) the electro-anatomic mapping system 902 (as depicted in FIG. 1) to wait for confirmation (such as, an indication signal provided by, or from, a user or operator, such as via a keyboard or other suitable input device, etc.). The confirmation indicates that a first medical device 101 is positioned at the first stationary position 201 located proximate to a biological wall 802 of (located within) a patient 800 (in which the first medical device 101 is (preferably) configured to be inserted into the patient 800).

Referring to the embodiments as depicted in FIG. 2 and FIG. 3, the method also includes utilizing (once the confirmation has been received) the electro-anatomic mapping system 902 (as depicted in FIG. 1) to transmit a first reference signal 401 to the first medical device 101 (while the first medical device 101 is kept positioned at the first stationary position 201). The first medical device 101 is maintained stationary relative to the first stationary position 201 or relative to the patient 800 and/or the biological wall 802.

Referring to the embodiments as depicted in FIG. 2 and FIG. 4, the method also includes utilizing the electro-anatomic mapping system 902 (as depicted in FIG. 1) to receive a first reference response signal 501 from the first medical device 101 (this is done while the first medical device 101 is kept positioned at the first stationary position 201. The first medical device 101 transmits, in use, the first reference response signal 501 (to the electro-anatomic mapping system 902) in response to the first medical device 101 receiving, in use, the first reference signal 401 from the electro-anatomic mapping system 902. The first reference response signal 501 is configured to be utilized by the electro-anatomic mapping system 902 for the formation (manufacture, generation) of a first medical image. The first medical image may display or show the biological wall 802 of the patient 800, which is to be displayed or depicted on a display device (known and not depicted) of the electro-anatomic mapping system 902.

Referring to the embodiment as depicted in FIG. 5, the method also includes utilizing the electro-anatomic mapping system 902 (as depicted in FIG. 1) to wait for confirmation (such as, an indication signal provided by (or from) a user or operator, such as via a keyboard or other suitable input device, etc.). The confirmation indicates that a second medical device 102 is positioned, and activated, at a noise-source position 202 located (positioned) relative to the first stationary position 201 and located relative (proximate) to the biological wall 802 of the patient 800 (this is done while the first medical device 101 is kept positioned at the first stationary position 201). The second medical device 102 is, preferably, configured to be inserted into the patient 800 (as depicted in FIG. 1).

Referring to the embodiments as depicted in FIG. 5 and FIG. 6, the method also includes utilizing the electro-anatomic mapping system 902 (as depicted in FIG. 1) to wait for confirmation (such as, an indication signal provided by (or from) a user or operator, such as via a keyboard or other suitable input device, etc.). The confirmation indicates that the second medical device 102 transmitted, in use, a second medical-device signal 302 toward the first medical device 101 (this is done while the first medical device 101 is kept positioned at the first stationary position 201, and while the second medical device 102 is kept positioned at the noise-source position 202). The second medical-device signal 302 may include, for instance, an amount of electromagnetic energy, radio frequency energy, etc., at a relatively low level or at an amount utilizable for cutting or forming a hole through the biological wall 802 but is not yet positioned and utilized for such purposes or deployment.

Referring to the embodiments as depicted in FIG. 5 and FIG. 7, the method also includes utilizing the electro-anatomic mapping system 902 (as depicted in FIG. 1) to receive a second reference response signal 502 from the first medical device 101. The second reference response signal 502 is configured to be utilized by the electro-anatomic mapping system 902 for forming (in a process for formation of) a second medical image of the biological wall 802 of the patient 800. The second medical image is to be displayed on the display device of the electro-anatomic mapping system 902. The second medical image (in use or as depicted) depicts image noise interference resulting from activation of the second medical device 102 positioned at the noise-source position 202 (while the first medical device 101 is kept positioned at the first stationary position). The first medical device 101 transmits, in use, the second reference response signal 502 (to the electro-anatomic mapping system 902) in response to the first medical device 101 receiving (A) the first reference signal 401 from the electro-anatomic mapping system 902, and (B) the second medical-device signal 302 from the second medical device 102.

Referring to the embodiments as depicted in FIG. 5 and FIG. 8, the method also includes utilizing the electro-anatomic mapping system 902 (as depicted in FIG. 1) to identify (compute) noise-correction datum 304 to be utilized for the generation of a relatively less noisier (less noisy, noise free) medical image by the electro-anatomic mapping system 902. The noise-correction datum 304 is a result of electromagnetic interaction (electromagnetic interference) between (A) the second medical-device signal 302, which was emitted by the second medical device 102 at the noise-source position 202, and (B) the first medical device 101. Preferably, the noise-correction datum 304 is computed, such as by the electro-anatomic mapping system 902, by a signal processing operation including subtraction between the second reference response signal 502 and the first reference response signal 501; in this manner, thereby, identification of the noise-correction datum 304 may be performed. The noise-correction datum 304 represents unwanted signal interference between (A) activation of the second medical device 102, and (B) utilization of the first medical device 101.

Referring to the embodiment as depicted in FIG. 9, the method also includes utilizing the electro-anatomic mapping system 902 (as depicted in FIG. 1) to wait for confirmation (such as, an indication signal provided by (or from) a user or operator, such as via a keyboard or other suitable input device, etc.). The confirmation indicates that the second medical device 102 is deactivated and moved away from the noise-source position 202 to a proximate position 204 located closer to the biological wall 802 of the patient 800 (while the first medical device 101 is kept positioned at the first stationary position 201).

Referring to the embodiments as depicted in FIG. 10 and FIG. 11, the method also includes utilizing the electro-anatomic mapping system 902 (as depicted in FIG. 1) to receive a third reference response signal 503 from the first medical device 101 (while the first medical device 101 is kept positioned at the first stationary position 201, and while the second medical device 102 is positioned at a wall-contact position 206). The wall-contact position 206 is located on a surface of the biological wall 802 of the patient 800. The wall-contact position 206 is positioned in a spaced-apart relationship relative to the noise-source position 202. The first medical device 101 transmits, in use, the third reference response signal 503 in response to the first medical device 101 receiving, in use, the second medical-device signal 302 from the second medical device 102 (preferably while the second medical device 102 is positioned at the wall-contact position 206).

Referring to the embodiments as depicted in FIG. 10 and FIG. 12, the method also includes utilizing the electro-anatomic mapping system 902 (as depicted in FIG. 1) to remove (compute, subtract), at least in part, signal interference from the third reference response signal 503. The third reference response signal 503 was provided by the first medical device 101 in response to receiving, in use, the second medical-device signal 302. Signal interference is imparted (created) by activation of the second medical device 102 (at the wall-contact position 206) while the second medical device 102 (in use) burns or forms a wall passageway 804 through the biological wall 802 at the wall-contact position 206 (as depicted in FIG. 10). Preferably, removal (subtraction), at least in part, of signal interference includes subtracting the noise-correction datum 304 (which was computed, from the third reference response signal 503).

Figure 14:
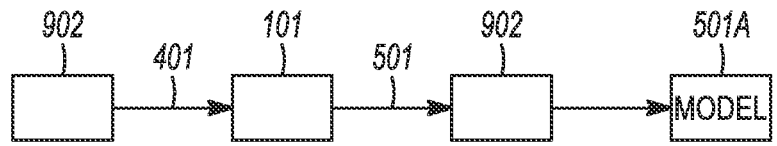
FIG. 14, FIG. 15 and FIG. 16 depict schematic views of embodiments of the electro-anatomic mapping system of FIG. 1.
Figure 15:
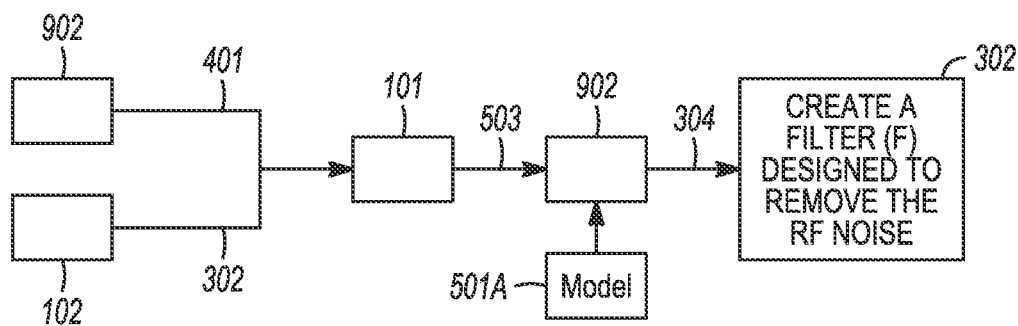
Figure 16:
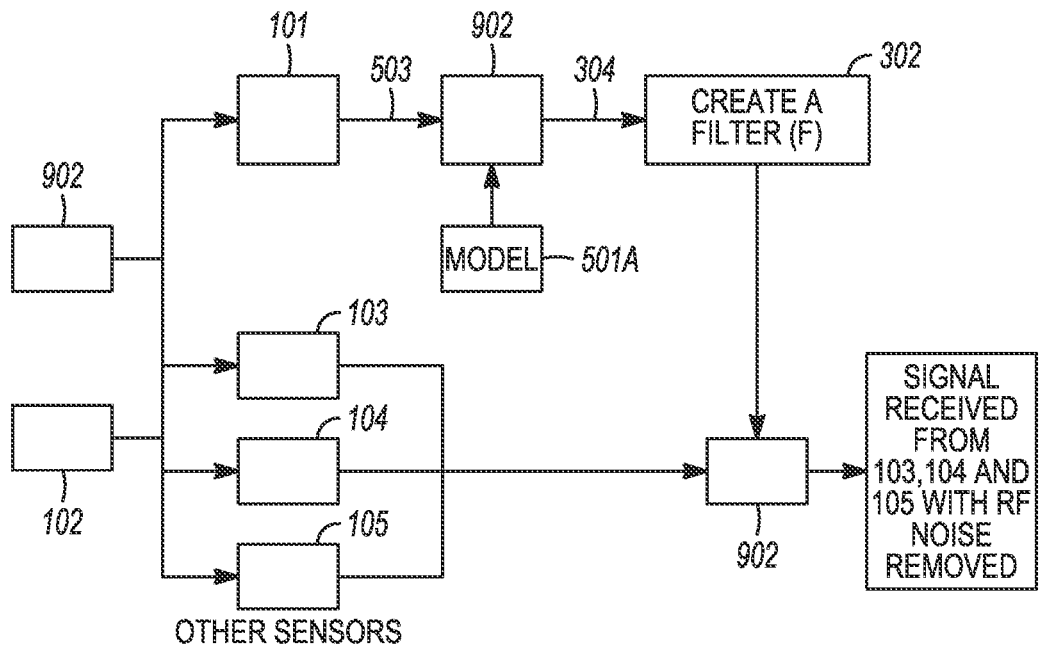

FIG. 14, FIG. 15 and FIG. 16 depict schematic views of embodiments of the electro-anatomic mapping system 902 of FIG. 1.

Referring to the embodiment as depicted in FIG. 14, the electro-anatomic mapping system 902 transmits, in use, the first reference signal 401 to the first medical device 101. In response, the first medical device 101 transmits, in use, the first reference response signal 501 back to the electro-anatomic mapping system 902. The electro-anatomic mapping system 902 is configured to use (read, receive) the first reference response signal 501, and to compute (form, create) a reference signal model 501A. The reference signal model 501A is (represents) a copy of the first reference response signal 501, or may be some other equivalent representation (e.g. frequency and phase components of a signal). For all intents and purposes, the reference signal model 501A is equivalent to the first reference response signal 501 as long as the properties (e.g. spatial positioning, etc.) of the electro-anatomic mapping system 902 and the first medical device 101 remain constant. It will be appreciated that any suitable algorithm (computation operations) may be utilized for computing (generating) the reference signal model 501A. For instance, one algorithm way includes performing (executing) a Fourier transform on the first reference response signal 501, and saving (retaining) the frequency components (including magnitude and phase for the frequency components). It will be appreciated that the reference signal model 501A may be computed by another computing system or by the electro-anatomic mapping system 902 (either approach may be acceptable).

Referring to the embodiment as depicted in FIG. 15, the electro-anatomic mapping system 902 (continues) to transmit the first reference signal 401 to the first medical device 101. The second medical device 102 is treated as a noise source (such as, a radio frequency puncture device (that is, initially turned OFF or deactivated). The second medical device 102 is positioned against (proximate to) the biological wall of the heart of the patient. The second medical device 102 is activated for cutting (forming a hole) through the biological wall of the heart. The second medical device 102 transmits (once it is activated) the second medical-device signal 302 (to be treated as the noise signal) to the first medical device 101 while the first reference signal 401 is continued to be transmitted to the first medical device 101. The first medical device 101 receives both the first reference signal 401 (from the electro-anatomic mapping system 902) and the second medical-device signal 302 (from the second medical device 102). In response to receiving both signals, the first medical device 101 transmits, in use, the third reference response signal 503 back to the electro-anatomic mapping system 902. The electro-anatomic mapping system 902 receives the third reference response signal 503 from the first medical device 101. In response to the second medical device 102 being activated, the electro-anatomic mapping system 902 also receives (inputs, reads) the reference signal model 501A (the reference signal model 501A is derived from the embodiment as depicted in FIG. 14). The electro-anatomic mapping system 902 computes the noise-correction datum 304. The noise-correction datum 304 is isolated (computed) or identified by evaluating (comparing) the third reference response signal 503 with the reference signal model 501A (such as, by subtraction and/or other equivalent algorithm). A noise filter (F) is computed based on the noise-correction datum 304. The noise filter (F) is configured to remove, at least in part, the contribution of the second medical-device signal 302 (from the medical image to be formed or generated and displayed by the electro-anatomic mapping system 902). The electro-anatomic mapping system 902 may be configured to compute the noise-correction datum 304. It will be appreciated that the electro-anatomic mapping system 902 (or other computing system) may be configured to identify (compute, isolate) the noise-correction datum 304 by evaluating (comparing) the third reference response signal 503 with the reference signal model 501A. The noise filter (F) may be computed based on the noise-correction datum 304. An approach to achieve this computation may include a subtraction algorithm, similar to the manner in which the noise-correction datum 304 may be computed.

Referring to the embodiment as depicted in FIG. 16, the electro-anatomic mapping system 902 may be required to interact with several additional medical device assemblies (such as, the first medical device 101, the second medical device 102, a third medical device 103, a fourth medical device 104 and a fifth medical device 105, etc.). The third medical device 103, the fourth medical device 104 and the fifth medical device 105 do not have the constraint of being fixed in position (relative to the electro-anatomic mapping system 902). The third medical device 103, the fourth medical device 104 and the fifth medical device 105 are each movable relative to the electro-anatomic mapping system 902. For this case, the filter (F) is used, by the electro-anatomic mapping system 902, to remove the noise originating from the second medical device 102 and transmitted through the third medical device 103, the fourth medical device 104 and the fifth medical device 105. It will be appreciated that the resulting noise from the third medical device 103, the fourth medical device 104 and the fifth medical device 105 may be similar (but not the same).

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all of the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus, comprising:
   an electro-anatomical mapping system, including:
   a processor assembly; and
   a non-transitory computer-readable storage medium including computer-executable instructions to control the processor assembly to:
      receive a first reference response signal from a first medical device at a first position proximate a biological wall of a patient, the first reference response signal for use with the electro-anatomical mapping system to form a first image;
      receive a second reference response signal from the first medical device at the first position, the second reference response signal for use with the electro-anatomical mapping system to form a second image, wherein the second reference response signal includes a first image noise interference from a second medical device activated at a noise-source position relative to the first position;
      determine a noise-correction datum based on the first reference response signal and the second reference response signal;
      receive a third reference response signal from the first medical device at the first position wherein the third reference response signal includes a second image noise interference from the second medical device activated at a wall-contact position relative to the first position to form an opening in the biological wall; and
      apply the noise correction datum to remove the second image noise interference from the third reference response signal; and
      transmit a fourth reference response signal to a display screen of electro-anatomical mapping system to form a third image representing the second medical device activated at the noise source position without the first image noise interference.

2. The apparatus of claim 1, wherein the first reference response signal is received in response to a first confirmation signal that the first medical device is at the first position.

3. The apparatus of claim 1, wherein the second reference response signal is received in response to a second confirmation signal that the second medical device is at the noise-source position and activated and the first medical device is at the first position.

4. The apparatus of claim 1, and further comprising an instruction to determine that the second medical device is deactivated and moving from the noise-source position to the wall contact position and the first medical device is at the first position.

5. The apparatus of claim 1, wherein the third reference response signal is received in response to a third confirmation signal that the second medical device is at the wall-contact position and activated and the first medical device is at the first position.

6. The apparatus of claim 1, and further comprising an instruction to compute a noise filter based on the noise correction datum.

7. The apparatus of claim 6, and further comprising an instruction to apply the noise filter to other medical device assemblies.

8. The apparatus of claim 1, wherein the noise correction datum is related to electromagnetic interference from the activated second medical device.

9. The apparatus of claim 1, wherein the instruction to apply the noise correction datum includes an instruction to subtract the noise correction data from the third reference response signal.

10. The apparatus of claim 1, wherein the fourth reference response signal is configured to be depicted on a display device by the electro-anatomical mapping system.

11. A method for use with an electro-anatomical mapping system, the method comprising:
    moving a first medical device to a first position proximate a biological wall of a patient receiving a first reference response signal from a first medical device at a first position proximate a biological wall of a patient, the first reference response signal for use with the electro-anatomical mapping system to form a first image;
    moving a second medical device to a noise source position relative to the first position;
    activating the second medical device at the noise source position;
    receiving a second reference response signal from the first medical device at the first position, the second reference response signal for use with the electro-anatomical mapping system to form a second image, wherein the second reference response signal includes a first image noise interference from the second medical device activated at the noise-source position relative to the first position;
    determining a noise-correction datum based on the first reference response signal and the second reference response signal;
    moving the second medical device to a wall contact position relative to the first position;

activating the second medical device at the wall contact position to form an opening in the biological wall;

receiving a third reference response signal from the first medical device at the first position wherein the third reference response signal includes a second image noise interference from the second medical device activated at the wall-contact position relative to the first position to form the opening in the biological wall; and applying the noise correction datum to remove the second image noise interference from the third reference response signal and generate a fourth reference response signal for use with the electro-anatomical mapping system to form a third image.

12. The method of claim 11, wherein the first reference response signal is received in response to a first confirmation signal that the first medical device is at the first position.

13. The method of claim 11, wherein the second reference response signal is received in response to a second confirmation signal that the second medical device is at the noise-source position and activated and the first medical device is at the first position.

14. The method of claim 11, and further comprising determining that the second medical device is deactivated and in motion from the noise-source position to the wall contact position and that the first medical device is at the first position.

15. The method of claim 11, wherein the third reference response signal is received in response to a third confirmation signal that the second medical device is at the wall-contact position and activated and the first medical device is at the first position.

16. The method of claim 11, and further comprising generating a noise filter based on the noise correction datum.

17. The method of claim 16, and further comprising applying the noise filter to other medical device assemblies using the electro-anatomical mapping system.

18. The method of claim 16, wherein the noise correction datum is related to electromagnetic interference from the activated second medical device.

19. The method of claim 11, wherein applying the noise correction datum includes subtracting the noise correction data from the third reference response signal.

20. The method of claim 11, and further comprising depicting an image for display based on the fourth reference response signal.

* * * * *